United States Patent [19]
Dyer et al.

[11] Patent Number: 5,871,906
[45] Date of Patent: Feb. 16, 1999

[54] METHOD FOR DETECTION OF AMPLIFIED NUCLEIC ACID PRODUCTS AND RELATED DIAGNOSTIC ASSAYS

[75] Inventors: David W. Dyer; Morris Bud Nelson, both of Buffalo; Anthony A. Campagnari, Hamburg, all of N.Y.

[73] Assignee: The Research Foundation of State University of New York, Amherst, N.Y.

[21] Appl. No.: 789,351

[22] Filed: Nov. 8, 1991

[51] Int. Cl.$^6$ .............................. C12Q 1/68; C12P 19/34
[52] U.S. Cl. .................................. 435/6; 935/77; 935/78
[58] Field of Search ................................. 435/6, 91, 91.2

[56] References Cited

U.S. PATENT DOCUMENTS 4,851,331   7/1989   Vary et al. .................................. 435/6
4,965,188  10/1990   Mullis et al. .............................. 435/91

Primary Examiner—Lisa B. Arthur
Attorney, Agent, or Firm—Hodgson, Russ, Andrews, Woods & Goodyear, LLP

[57] ABSTRACT

Disclosed is a method for detecting the presence or absence of amplified nucleic acid products. The method comprises the addition of hapten-labeled nucleotide or target molecule-labeled nucleotide to an amplification reaction and after the amplification process assaying for the presence of nucleic acid products having incorporated hapten-labeled nucleotide or target molecule-labeled nucleotide. Immobilization and detection of the label is accomplished using an affinity molecule that binds specifically to the hapten or target molecule. Thus, detection of amplified nucleic acid products is direct and does not require hybridization with a labeled specific probe.

19 Claims, 5 Drawing Sheets

METHOD FOR DETECTION OF AMPLIFIED NUCLEIC ACID PRODUCTS AND RELATED DIAGNOSTIC ASSAYS

BACKGROUND OF THE INVENTION

1. Field of the Invention

This invention relates generally to the detection of amplified nucleic acid products, and more specifically to a method of directly detecting the presence or absence of amplified nucleic acid product containing incorporated label molecules.

2. Description of the Background and Related Art

Recent advances in molecular biologic techniques have provided several means for enzymatically amplifying nucleic acid sequences. Currently the most commonly used method, PCR (Polymerase Chain Reaction, Cetus Corporation) involves the use of Taq Polymerase, known sequences as primers, and heating cycles which separate the replicating deoxyribonucleic acid (DNA) strands, in exponentially amplifying a gene of interest. Other amplification methods are currently under development. Examples include the ligase chain reaction (LCR, BioTechnica International) which utilizes DNA ligase, and a probe consisting of two halves of a segment of DNA that is complementary to the sequence of the DNA to be amplified, in mediating DNA amplification. Methods for amplifying genes are not limited to DNA only. Using the enzyme QB replicase (Gene-Trak Systems), and a ribonucleic acid (RNA) sequence template attached to a probe complementary to the DNA to be copied, the DNA becomes a template for exponential production of complementary RNA. Nucleic Acid Sequence-Based Amplification (NASBA, Cangene) can be performed on RNA or DNA as the nucleic acid sequence to be repeatedly copied.

Gene amplification techniques are powerful tools with potential to be used for quicker, earlier, and more definitive diagnosis of infectious diseases, genetic disease, and cancers. For example, PCR Protocols: A Guide to Methods and Applications ( © 1990, Academic Press) describes the use of PCR in the detection of human immunodeficiency virus, hepatitis B virus, genital human papillomaviruses, cytomegalovirus, enteroviruses, B-cell lymphoma, and retinoblastoma. However, some of the amplification techniques such as PCR suffer because they lack fidelity and thus extraneous sequences,i.e. DNA other than the desired sequence, may be amplified. Such possibilities hinder the application to acceptance in diagnostics. Thus, conventional methods for the detection of amplified nucleic acid products require post-amplification specificity by utilizing a post-amplification hybridization technique such as agarose gel electrophoresis with subsequent Southern blot analyses. The following is a list of relevant prior art along with a brief description of each:

U.S. Pat. No. 4,683,195, issued Jul. 28,1987, discloses a process for detecting nucleic acid sequences in a sample suspected to contain the nucleic acid sequences by an amplification process using a chain reaction in which primer extension products are produced. Detection of genetic diseases is described by analyzing the amplified product using radioactive or non-radioactive probes via a Southern blotting technique. In another embodiment a small amount of DNA is amplified to a convenient level first, then further cycles are performed wherein the nucleotide derivatives, which are readily detectable, are incorporated directly into the final product and analyzed by a method such as restriction and electrophoretic separation.

Lundeberg et al., BioTechniques (1991) 10:68–75, describe a method of detecting amplified DNA by biotinylated primers and competitive inhibition using a lac operator sequence incorporated into amplified DNA and detection of the amplified competitor DNA using a fusion protein comprising beta-galactosidase and the LacI repressor.

Dahlen et al., Journal of Microbiology (1991) 29:798–804, describe a time-resolved fluorescence-based hybridization assay. Following amplification by PCR, two oligonucleotide probes, one biotinylated and one labeled with europium, are hybridized to the amplified products. The sandwich hybrids are collected in a microtitration well coated with streptavidin, and the bound europium is measured in a time-resolved fluorometer.

By the term "hapten or target molecule" is meant, for the purposes of the specification and claims, molecules useful as molecular labels which are too small to elicit by themselves an immunological response but are capable of binding with antibodies, and also encompasses small molecules which can serve as molecular labels by virtue of their ability to interact with affinity molecules other than antibody.

U.S. Pat. No. 4,683,195, Lundberg et al. and Dahlen et al., describe methods for the detection of amplified DNA which rely on post-amplification specificity utilizing hybridization with one or more labeled oligonucleotide probes. These detection-by-hybridization systems require the need to a add a label, such as hapten or target molecules, to each primer. Further, a limited amount of label, ranging from one to several molecules per probe, is incorporated into the probe thereby limiting the sensitivity that can be achieved in subsequent detection processes. The method of the present invention to detect amplified nucleic acid products relies on the sensitivity and specificity of the amplification process, since the hapten-labeled nucleotide or target molecule-labeled nucleotides are incorporated directly into the amplified product, rather than post-amplification specificity. For example, the sensitivity and specificity of the amplification process depend critically upon the specificity of the primers and the amplification reaction conditions. Once the primers and amplification reactions have been optimized, these detection-by-hybridization systems are unnecessary. A potential problem for detection of amplified nucleic acid products using the method of present invention is that in an amplification process, such as by PCR, false-positives could result, for example, from physical carryover of amplified DNA from sample to sample in multi-sample analyses. However, physical precautions, procedural safeguards, new equipment and modification of the processes have been, and continue to be, implemented to minimize potential for false-positive results. Thus, the art has now advanced to where it may be possible to omit post-amplification specificity. Further, the method of the present invention incorporates hapten-labeled nucleotide or target molecule-labeled nucleotide directly into the amplified product, in addition to the advantages of omitting pretreatment steps to incorporate label into each primer and the subsequent post-hybridization steps required for detection, there is increased sensitivity because significantly more molecules containing label can be incorporated into the amplified nucleic acid product than can be incorporated onto an oligonucleotide.

Each of the above cited references discloses a diagnostic system utilizing post-amplification specificity for detection of amplified DNA products. Use of agarose gel electrophoresis followed by Southern blot analysis, as disclosed in U.S. Pat. No. 4,683,195, is time consuming, as well as being unsuitable for large scale commercial applications. Lundeberg et al. and Dahlen et al. Disclose a diagnostic system similar to the system described in the present invention in that they all utilize a solid-phase approach to detect immobilized amplified nucleic acid products. In addition to post-hybridization steps, the system disclosed by Lundeburg et al. requires synthesis of a competitor strand of DNA identical to the target DNA to be analyzed. The competitor DNA also requires in-vitro mutagenesis to introduce into that fragment the lac operator sequence. The biotin label is used to bind the competitor strand to the solid support via the affinity molecule streptavidin, but detection is accomplished on the basis of the interaction of the lac operator site of the competitive strand of DNA with the laci repressor protein and β-galactosidase. Note that in the system of the present invention the label, hapten or target molecule, serves a dual purpose by binding the amplified nucleic acid products to the immobilized affinity molecules, as well as interacting with conjugate and substrate in the detection process. In contrast, in the system of Lundeburg et al., the target molecule incorporated into the hybridization probe is only used for binding to the immobilized affinity molecule. The system of the present invention involves direct detection of the amplified nucleic acid product rather than detection of a competitor strand as disclosed by Lundeburg et al. In addition, the system described in the present invention has increased sensitivity, when compared to the system described by Lundeburg et al., since multiple molecules of label are incorporated into the amplified product thereby enhancing the amount of binding to the immobilized affinity molecules, and enhancing calorimetric detection because more incorporated label is available for interaction with conjugate and substrate.

The system described by Dahlen et al. also utilizes a solid phase approach. However, they teach the use of two probes, each containing a different label, in the post-hybridization process leading to detection. One probe is labeled with a target molecule that is used to interact with immobilized affinity molecules, while another probe is labeled with europium ($Eu^{3+}$) to be detected in a time-resolved fluorometer. As noted above, the system of the present invention omits the post-hybridization process and utilizes only a single species of label which serves to bind the amplified nucleic acid products to the immobilized affinity molecules, and to interact with conjugate and substrate in the detection process.

In another embodiment of U.S. Pat. No. 4,683,195 is disclosed the incorporation of readily detectable nucleotide derivatives into the final amplified DNA product. The method of the present invention differs in that the step of first amplifying a small amount of DNA to a convenient level, as taught by U.S. Pat. No. 4,683,195, is omitted. In the method of the present invention, the hapten-labeled nucleotide or target molecule—labeled nucleotide is added to the initial reaction thereby obviating the need to stop the reaction. Secondly, the method of the present invention is directed to the detection of amplified nucleic acid products using any one of several available amplification processes and includes the detection of RNA as well as DNA. Only the detection of DNA, amplified by the polymerase chain reaction, is disclosed in U.S. Pat. No. 4,683,195. The method of the present invention provides for an enzyme-linked immunosorbent assay (ELISA)-based system for detection which utilizes a single species of label, hapten or target molecule, that serves to bind the amplified nucleic acid products to immobilized affinity molecules, and to interact with conjugate and substrate in the detection process. Such an assay is well-suited for multi-sample analyses in both clinical and research applications.

Therefore, a method for the detection of amplified nucleic acid products that is direct (not requiring hybridization), simple, quick, and adaptable to multi-sample analyses, is desirable. A method, as such, will greatly facilitate biomedicine in the early detection and diagnoses of infectious agents, cancer, and genetic disease.

SUMMARY OF THE INVENTION

Accordingly, a primary objective of the present invention is to provide a method for the detection of amplified nucleic acid products that is direct, simple, quick, and adaptable to multi-sample analyses.

Another object of the invention is to provide a method suitable for incorporation into various forms of diagnostic assays for the detection of infectious agents, cancer, and genetic disease.

A further object of the invention is the development of diagnostic kits, employing this method, to be used in research and clinical settings for the detection of infectious agents, cancer, and genetic disease.

In summary, the above is accomplished by providing a method wherein a nucleic acid sequence of interest is amplified, and the resultant copies incorporate hapten-labeled nucleotide or target molecule-labeled nucleotide into the sequence. A solid support system containing immobilized affinity molecules specific for the hapten or target molecule, is used to capture the amplified copies via the specific interaction between the affinity and incorporated hapten or target molecule-labeled nucleotide. A conjugate comprising the affinity molecules conjugated to reporter compounds may be used to facilitate visualization of the presence of amplified nucleic acid products.

BRIEF DESCRIPTION OF THE INVENTION

A more complete appreciation of the invention, and its many attendant advantages thereof, and a better understanding of its features may follow by referring to the detailed description in connection with the accompanying figures, wherein:

FIG. 1 and 1B are fragmentary side view of a well of an ELISA (enzyme-linked immunosorbent assay)-type format depicting a series of steps for the detection of amplified nucleic acid products, if present in the sample (FIG. 1A), or in the absence of amplified product in the sample (FIG. 1B), using the digoxygenin/anti-digoxygenin system.

FIG. 2 and 2B are fragmentary side view of a well of an ELISA-type format depicting a series of steps for the detection of amplified nucleic acid products, if present in the sample (FIG. 1A), or in the absence of amplified product in the sample (FIG. 1B), using the biotin/avidin system.

DETAILED DESCRIPTION

The method for the detection of amplified nucleic acid products of the present invention includes the use of immobilized affinity molecules capable of binding (capture) hapten-labeled nucleotide or target molecule-labeled nucleotide that have been incorporated into amplified nucleic acid products during strand synthesis in an amplification process; and reaction of the unbound incorporated hapten-labeled nucleotide or target molecule-labeled nucleotide to affinity molecules conjugated to reporter compounds or enzymes which are visualized directly or by substrate color development. Steps in the process of the present invention include: immobilization of the affinity molecules to a solid support by covalent coupling or non-covalent adsorption; removal of unbound affinity molecules from the solid support using a wash step; blocking the surface areas of the solid support, not bound by affinity molecules, to prevent non-specific binding to the solid support surface by nucleic acids that may be present in the amplification reaction sample to be analyzed; addition and incubation of the sample to be analyzed with the modified solid support to allow reaction between the affinity molecules and hapten or target molecules contained in the added sample; a second wash step to remove nonspecifically bound hapten-labeled nucleotide or target molecule-labeled nucleotide, molecules not captured by the affinity molecules, as well as to remove other components, other than amplified nucleic acids, contained in the amplification reaction sample; addition and incubation of an affinity molecule conjugate to allow reaction with any unbound incorporated hapten or target molecules remaining from the preceding sequential steps, wherein said conjugate consists of either reporter molecules that can be directly visualized or enzyme that requires interaction with substrate for color development; a third wash step to remove unbound conjugate; and either direct visualization of the full process, or addition and incubation of substrate to allow reaction with any bound affinity conjugate present, resulting in color development to facilitate visualization of the full process.

PREFERRED EMBODIMENTS

The following three examples are diagnostic assays which incorporate the method of the present invention. These diagnostic assays will be available in two different formats. In the first format, a nucleic acid probe, to be used in the amplification process and specific for the nucleic acid sequence to be amplified, will be provided in a diagnostic kit. Therefore, diagnostic kits will be tailored to assay for a specific infectious agent, cancer, or genetic disease. In the second format, these diagnostic kits will be available without the specific probe to be used in the amplification process. The user of the kit will provide his/her own probe directed to the nucleic acid sequence which is the object of the amplification reaction.

EXAMPLE A

The method of the present invention allows for the direct detection of amplified nucleic acids in samples subjected to a nucleic acid amplification technique. To facilitate direct detection, a hapten-labeled nucleotide or target molecule-labeled nucleotide are incorporated into the amplified nucleic acid products. Such a hapten or target molecule is digoxigenin, a steroid derived from digitalis plants. Digoxigenin is used to label one or more of the deoxynucleotide triphosphates (dNTPs) such as deoxyuridine triphosphate, dUTP (See Lion and Haas, 1990, Analytical Biochemistry, 188:335–337, hereby incorporated by reference). The amplification process would be performed according to the directions of the manufacturer. However, the reaction mixture would contain digoxigenin-labeled dUTP in addition to standard concentrations of deoxyadenine triphosphate, deoxycytosine triphosphate, and deoxythymine triphosphate (dATP, dCTP, and dTTP, respectively). If the nucleic acid sequence that is the object of the amplification process is present, then copies of that sequence will be synthesized in that reaction. These copies will be composed of the dNTPs present in the reaction mixture. Thus these copies will have incorporated as part of their molecular structure, the digoxigenin-labelled dUTP as depicted in FIG. 1. In this preferred embodiment of the present invention, an enzyme-linked immunosorbent assay (ELISA) or similar assay is utilized in detecting the amplified nucleic acid, if present in the sample, by specifically binding the incorporated digoxigenin. The detection method of the present invention comprises a first step in which the affinity molecule specific for digoxygenin, selected from the group consisting of anti-digoxygenin antibody, anti-digoxin antibody, and combinations thereof, is used to coat the wells of an ELISA plate. The attachment of the antibodies to plastic can be achieved by noncovalent or covalent means. There are many different protocols known to those skilled in the art to attach immunoglobulins, or fragments thereof, to the respective solid surface. Such protocols include preferential adsorption of the Fc portion of the antibody molecule during the coating process, allowing the Fab portion of the antibody molecule that contains the antigen binding or affinity sites to be more accessible, thus increasing the efficiency of antigen binding in the detection process.

To prepare the wells for subsequent addition of the sample to be analyzed, the wells must be washed extensively to remove residual unbound affinity molecules from the coating process. Non-specific sites, defined as uncoated surfaces within the well which could bind nonspecifically to components in the sample to be analyzed, are saturated or blocked to reduce background in the assay. Blocking agents may be selected from those known in the art such as bovine serum albumin (BSA), denatured salmon sperm DNA (optimum concentration about 20 ug/ml), gelatin, Tween-20, and combinations thereof. The blocking process would require the addition of a solution containing the blocking agent to the wells and subsequent incubation for a sufficient time as to saturate unbound sites. Conditions found to work well for the method of the present invention include incubating at ambient temperature (25° C.) for about 2 hours. After the blocking process, excess blocking agent is removed by washing the wells with buffer solution not containing blocking agent.

Figure 1A:
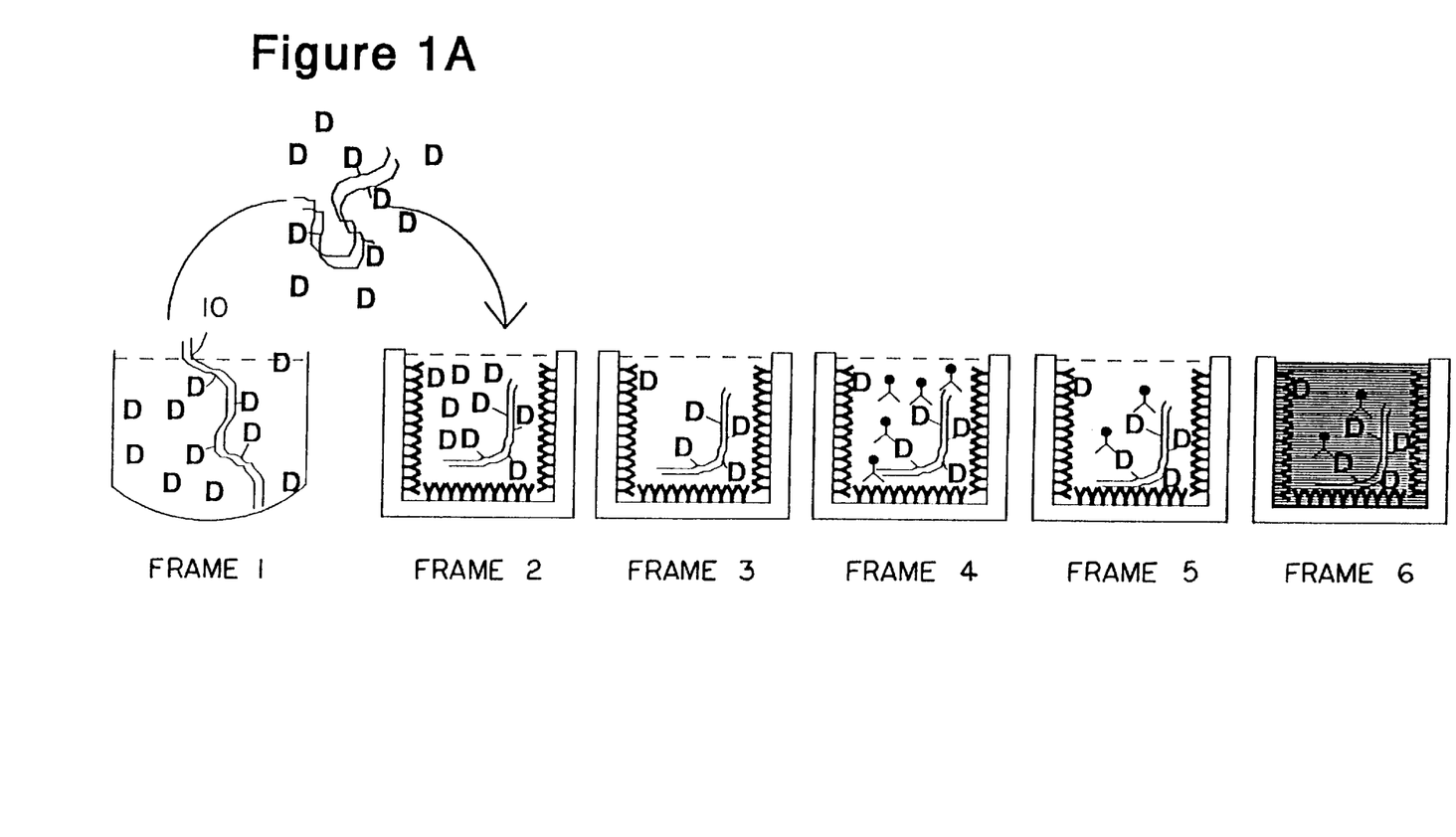

FIG. 1A, frame 2, shows a well of a microtiter plate, which would be incorporated in the diagnostic kit of the present invention, that has been coated with anti-digoxygenin antibody (Y), blocked with a blocking agent, and the sample to be analyzed has been added. FIG. 1A frame 1 shows a sample from an amplification reaction containing amplified DNA (10). The "D" in this figure represents digoxygenin-labelled dUTP incorporated into the amplified nucleic acid (digoxygenin-polymer) as well as representing unincorporated digoxygenin-labelled dUTP (digoxygeninmonomer). For purposes of illustration, the different components, including the affinity molecule and the copies of amplified nucleic acid, are shown in relatively small numbers whereas in actual practice hundreds to thousands of times the number shown are actually present. After an incubation process, for a time sufficient to allow binding to occur between the digoxygenin and the anti-digoxygenin antibody, the well is washed with a buffer solution to remove any unbound digoxygenin-monomer or -polymer as shown in FIG. 1A, frame 3. The next step involves the addition of a conjugate (λ) which will bind to unbound digoxygenin-polymer present in the well as shown FIG. 1A, frame 4. The conjugate consists of anti-digoxygenin antibodies coupled with one of the following reporter compounds: an enzyme, a chromophore, a fluorophore, or a marker. Examples of the reporter compounds, used to facilitate visualization, are alkaline phosphatase, peroxidase, fluorescein and rhodamine. The conjugate shown in this figure consists of anti-digoxygenin antibodies conjugated to alkaline phosphatase. Some of the conjugates require the addition of a calorimetric substrate to facilitate detection. Prior to detection or substrate addition, a wash step is required to remove any unbound conjugate from the well as shown in FIG. 1 frame 5. In this specific embodiment of the invention, the substrate comprises nitroblue tetrazolium salt (NBT) and 5-bromo-4-chloro-3-indolyl phosphate which will result in a color reaction to indicate the presence of amplified nucleic acid as illustrated in FIG. 1 frame 6.

Figure 1B:
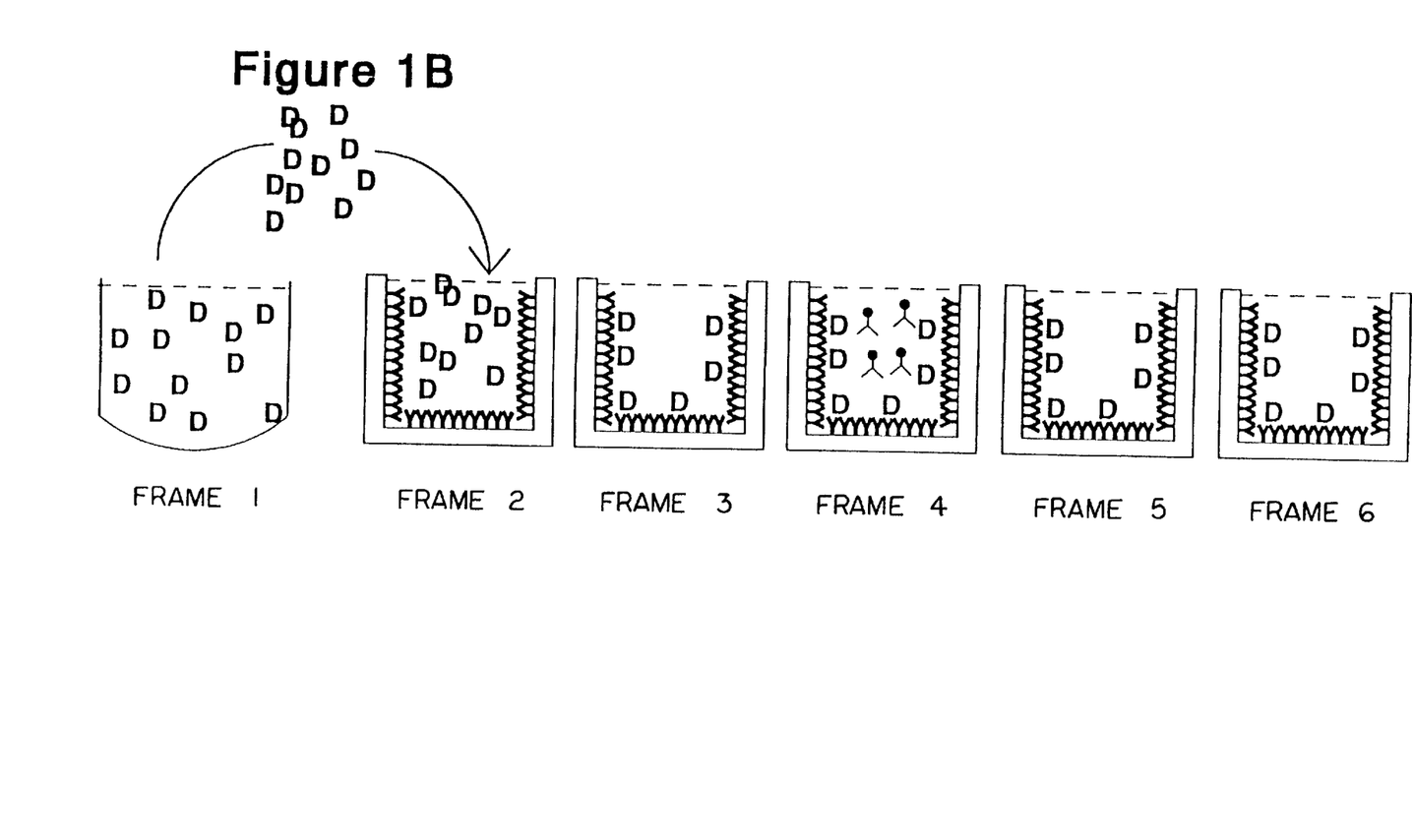

If there are no copies of amplified nucleic acid products in the sample, as depicted in FIG. 1B, frame 1, only the digoxygenin-monomer will bind to the anti-digoxygenin antibodies that coat the well as illustrated in FIG. 1B frame 2. A subsequent wash step, shown in FIG. 1B frame 3, will remove unbound digoxygenin-monomer. Since the digoxygenin-monomer is already bound by the anti-digoxygenin antibodies coating the plate, essentially no sites on the digoxygenin-monomer are available to the conjugate (λ) upon addition as shown in FIG. 1B frame 4. After the subsequent washing step (See FIG. 1B frame 5), there will be insufficient amounts of conjugate for interaction upon subsequent addition of substrate as shown in FIG. 1B frame 6; therefore there will be a low level or no detectable color change.

EXAMPLE B

A second embodiment of the present invention utilizes biotin as the hapten or target molecule to label dUTP. If the nucleic acid sequence that is the object of amplification is present, and biotin-labeled dUTP is included in the reaction mixture, then copies of the sequence will have incorporated biotin-labeled dUTP as part of their composition (See FIG. 2A frame 1). In this preferred embodiment of the present invention, an enzyme-linked immunosorbent assay (ELISA) or similar assay is utilized in detecting the amplified nucleic acid, if present in the sample, by specifically binding the incorporated biotin. The detection method of the present invention comprises a first step in which the affinity molecule specific for biotin, selected from the group consisting of avidin and streptavidin, is used to coat the wells of an ELISA plate. The attachment of the avidin to plastic can be achieved using non-covalent or covalent means known to those skilled in the art. The subsequent washing and blocking steps, to prepare for the addition of the sample to be assayed, are accomplished as previously described in detail in Example A.

Figure 2A:
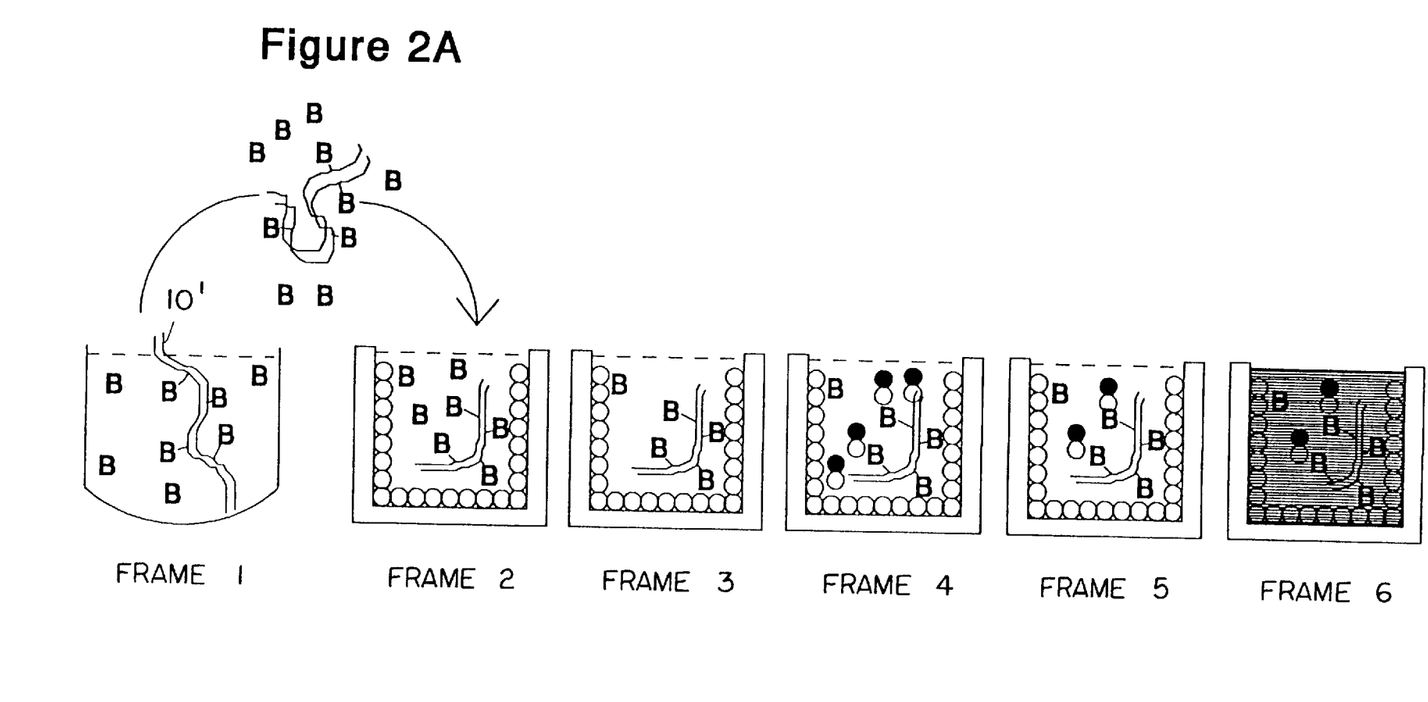

FIG. 2A frame 1 depicts a sample as containing amplified copies of the nucleic acid of interest (10'). FIG. 2A, frame 2, shows a well which has been coated with avidin affinity molecules (o), blocked with a blocking agent, and the sample to be analyzed has been added. The "B" in this figure represents biotin-labeled dUTP incorporated into the amplified nucleic acid (biotinpolymer) as well as representing unincorporated biotin-labeled dUTP (biotin-monomer). As described in Example A, the relatively small amounts of components shown in this figure are for purposes of simplifying the illustration only. After an incubation process, for a time sufficient to allow binding to occur between the biotin and avidin, the well is washed with a buffer solution to remove any unbound biotin-monomer or -polymer as shown in FIG. 2A, frame 3. The next step involves the addition of a conjugate (●o) which will bind to unbound biotin-polymer present in the well as shown FIG. 2A, frame 4. In this embodiment, the conjugate is selected from the group consisting of avidin and streptavidin, coupled to on of the following reporter compounds: an enzyme, a chromophore, a fluorophore or a marker. Examples of the reporter compounds are alkaline phosphatase, peroxidase, fluorescein and rhodamine. The conjugate shown in this figure consists of avidin conjugated to peroxidase. After the addition of avidin-peroxidase, and following an incubation period, a wash step is required to remove any unbound conjugate (See FIG. 2A frame 5). In this specific embodiment of the invention, the substrate comprises 4-chloro 1-naphthol, the addition of which results in a color reaction indicating the presence of amplified nucleic acid products, as shown in FIG. 2A frame 6.

Figure 2B:
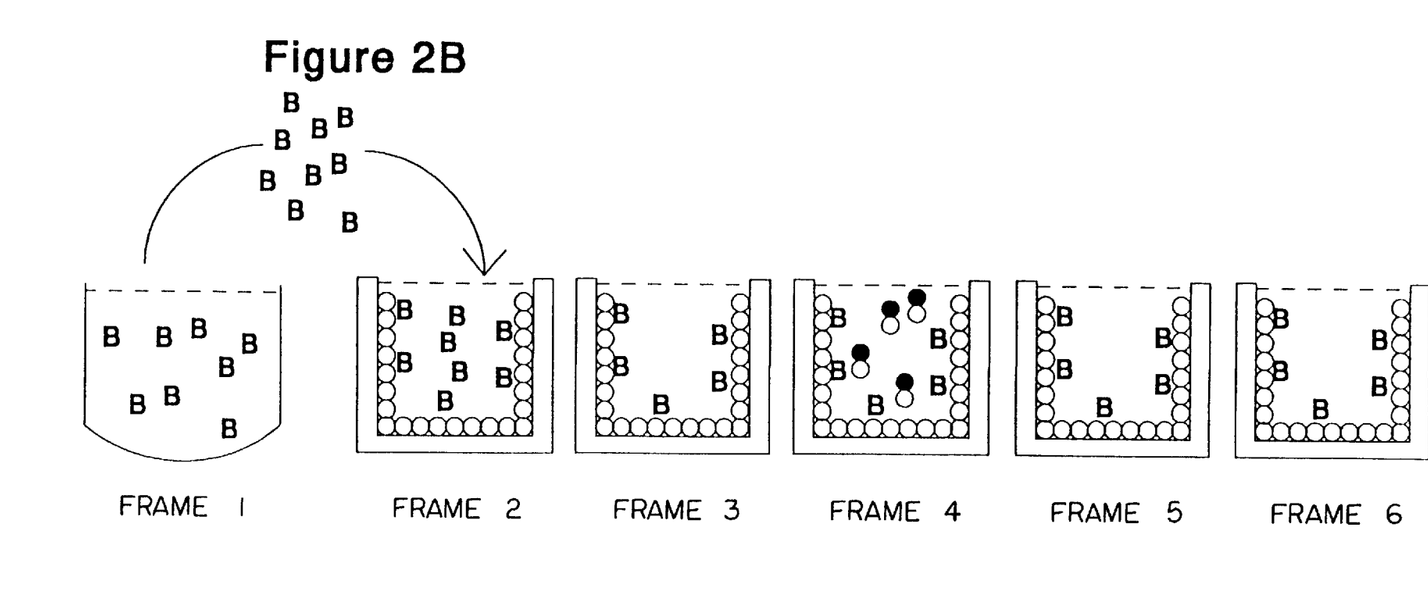

If there are no copies of amplified nucleic acid products in the sample, as depicted in FIG. 2B, frame 1, addition of the sample to the well will result in the biotin-monomer binding to the avidin coating the well (FIG. 2B frame 2). A subsequent wash step, shown in FIG. 2B frame 3, will remove unbound biotin-monomer. Since one molecule of biotin can only bind to one molecule of avidin, there are no sites available for the conjugate (FIG. 2B frame 4). After the subsequent washing step (FIG. 2B frame 5), there will be insufficient amounts of conjugate for the substrate to interact with, as shown in FIG. 2B frame 6. Therefore, there will be no detectable color change upon the addition of substrate.

EXAMPLE C

Figure 3:
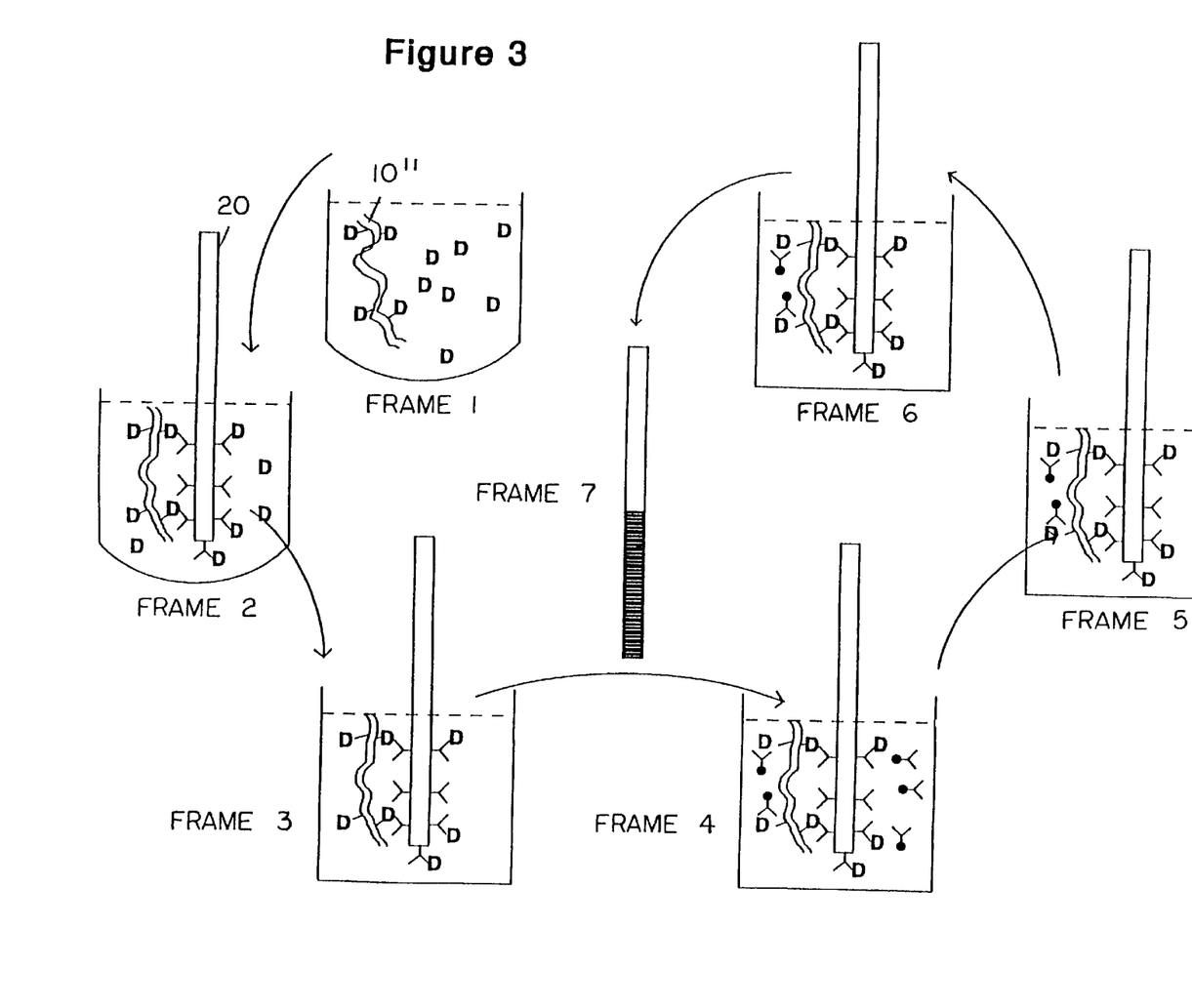
FIG. 3 is a diagram depicting the detection, by dipstick-type format, of amplified nucleic acid products, if present in the sample (A), or in the absence of amplified product in the sample (B).

The preferred means of assaying the methods described in Examples A and B was by ELISA. A second means, described hereinafter as the "dipstick detection system", is an simple and rapid alternative to detection by ELISA. The dipstick detection system is comprised of a dipstick (20), a long slender solid support means preferably of plastic material, and a series of vessels which house different solutions to be used in a step-wise, sequential manner as shown in FIG. 3. At one end of the dipstick will be affixed, by covalent or non-covalent means, affinity molecules selected from the group consisting of anti-digoxygenin antibodies, anti-digoxin antibodies, avidin and streptavidin. The amplification reaction will be carried out according to the manufacturer's instructions, except that hapten-labeled dUTP will be added as referred to in Examples A and B. The hapten, chosen for its specificity to its corresponding binding affinity molecule, is selected from the group consisting of digoxygenin and biotin. For illustration purposes, the dipstick detection system shown in FIG. 3 utilizes digoxygenin (D) as the hapten, and anti-digoxygenin antibodies (Y) as the affinity molecules and is depicted to show the presence of amplified copies of nucleic acid (10") in the sample. The pre-blocked dipstick may be incubated directly in the chamber wherein the amplification reaction occurred, thus obviating the need to remove the sample first before assaying (FIG. 3, frames 1 and 2). In the alternative, the sample may be removed to another vessel before the dipstick is inserted and incubated in the presence of the sample. Following this incubation, the dipstick is removed from the sample and inserted, incubated and swirled in a container containing a wash solution to remove any non-specifically bound DNA (FIG. 3 frame 3). The dipstick is removed from the wash solution and inserted into and incubated in the presence of conjugate contained within another vessel (FIG. 3 frame 4). The conjugate is selected from the group as described in detail in Examples A and B. In FIG. 3, frame 4, the conjugate depicted comprises anti-digoxygenin antibodies coupled to alkaline phosphatase. The dipstick is then washed again to remove any non-specifically bound conjugate (FIG. 3 frame 5) and inserted into and incubated in the presence of a substrate solution contained within yet another vessel (FIG. 3, frame 6). The development of a color reaction at the end of the dipstick, subsequent to the sequential steps of this detection system, is indicative of the presence of amplified copies of nucleic acid contained within the sample analyzed (FIG. 3, frame 7).

Although the present invention has been described in some detail by way of illustration and example for purposes of clarity of understanding, various modifications will become apparent to persons skilled in the art from the foregoing description and accompanying figures. Such modifications are intended to be included within the spirit of this application and within the scope of the appended claims.

What is claimed is:

1. An affinity-based method for detecting the presence or absence of copies of amplified nucleic acid sequence in samples from an amplification process comprising:
   (a) adding hapten-labeled nucleotide or target molecule-labeled nucleotide to the amplification reaction prior to the amplification process;
   (b) contacting a sample of the reaction mixture, after the amplification process, with immobilized affinity molecules which specifically binds the hapten label or target molecule label;
   (c) incubating the components from step (b) under conditions whereby the immobilized affinity molecules will bind to either unincorporated hapten-labeled nucleotide or target molecule-labeled nucleotide, or hapten-labeled nucleotide or target labeled nucleotide incorporated into copies of amplified nucleic acid sequence, whichever is contained in the sample;
   (d) adding a conjugate comprising affinity molecules coupled to a reporter compound to the components of step (c), wherein the affinity molecules of the conjugate are the same as the immobilized affinity molecules of step (b), and whereby the conjugate will bind to copies of nucleic acid sequence, if present in the sample, via incorporated hapten-labeled nucleotide or target molecule-labeled nucleotide not bound by the immobilized affinity molecules;
   (e) detecting the amount of conjugate bound in step (d);
   (f) relating the detection of bound conjugate to the presence or absence in the sample of copies of amplified nucleic acid sequence.

2. The method of claim 1 wherein the nucleotide is dUTP and the hapten or target molecule utilized as a label is selected from the group consisting of biotin and digoxygenin.

3. The method of claim 1 wherein the affinity molecules are selected from the group consisting of avidin, streptavidin, anti-digoxygenin antibodies, and anti-digoxin antibodies.

4. The method of claim 1 wherein the reporter compound is selected from the group consisting of an enzyme, a chromophore, and a fluorophore.

5. The method of claim 4 wherein the enzyme is selected from the group consisting of a peroxidase, beta-galactosidase, and alkaline phosphatase.

6. The method of claim 1 wherein the conjugate is an enzyme and further including:
   a) removing unbound conjugate, and
   b) adding a calorimetric substrate to facilitate visualization.

7. The method of claim 1 wherein the immobilized affinity molecules are attached to a solid phase by covalent or noncovalent means.

8. The method of claim 7 wherein the solid phase is treated after attachment of the affinity molecules so as to prevent non-specific binding by contents of the sample to areas of the solid phase not bound by affinity molecules.

9. The method of claim 7 wherein the solid phase is the well of a microtiter plate.

10. The method of claim 7 wherein the solid phase is a dipstick.

11. An affinity-based method for detecting the presence or absence of amplified nucleic acid products comprising:
    (a) utilizing a solid support system including immobilized affinity molecules for the capture of hapten-labeled nucleotide or target molecule-labeled nucleotide that have been incorporated into amplified nucleic acid products during strand synthesis in the amplification process; and
    (b) reacting the unbound incorporated hapten-labeled nucleotide or target molecule-labeled nucleotide to affinity molecules conjugated to reporter compounds which are visualized directly or by substrate development, wherein the conjugated affinity molecules are the same as the immobilized affinity molecules of step (a);
    (c) so that detection of the amplified nucleic acid products is direct and does not require hybridization by oligonucleotide probes in the detection process.

12. An affinity-based method for detecting the presence or absence of amplified nucleic acid sequence in samples from an amplification process comprising:
    (a) immobilizing affinity molecules to a solid support by covalent coupling or non-covalent adsorption;
    (b) removing unbound affinity molecules from the solid support;
    (c) blocking the surface areas of the solid support, not bound by afinity molecules, to prevent non-specific binding to the solid support by nucleic acids which may be present in he amplification reaction to be analyzed;
    (d) adding and incubating the sample to be analyzed with the modified solid support to allow reaction between the affinity molecules and hapten-labeled nucleotide or target molecule-labeled nucleotide contained in the sample;
    (e) removing the nonspecifically bound hapten-labeled nucleotide or target molecule-labeled nucleotide and molecules not captured by the affinity molecules together with other components, other than specifically bound amplified nucleic acids, contained in the amplification reaction sample;
    (f) adding and incubating an affinity molecule conjugate to allow reaction with any unbound incorporated hapten-labeled nucleotide or target molecule-labeled nucleotide remaining from the preceding steps, wherein the affinity molecules of the conjugate are the same as the immobilized affinity molecules;
    (g) removing unbound conjugate; and
    (h) providing color development to facilitate visualization of the entire process.

13. The method of claim 12, wherein said step b) of removing unbound affinity molecules is performed by washing.

14. The method of claim 12, wherein said step of removing nonspecifically bound hapten-labeled nucleotide or non-specifically bound target molecule-labeled nucleotide, and molecules not captured by the affinity molecules, is performed by washing.

15. The method of claim 12, wherein said conjugate comprises reporter compounds that can be directly visualized.

16. The method of claim 12, wherein said conjugate comprises an enzyme that requires interaction with a substrate for color development.

17. The method of claim 12, wherein said step of removing unbound conjugate is performed by washing.

18. The method of claim 12, wherein said step of providing color development is performed by direct visualization by the entire process.

19. The method of claim 12, wherein said step of providing color development comprises addition and incubation of substrate to allow reaction with any bound conjugate present.

* * * * *

UNITED STATES PATENT AND TRADEMARK OFFICE
CERTIFICATE OF CORRECTION

PATENT NO.   : 5,871,906
DATED        : February 16, 1999
INVENTOR(S)  : David W. Dyer; Morris Bud Nelson; Anthony A. Campagnari It is certified that error appears in the above-identified patent and that said Letters Patent is hereby corrected as shown below:

Col. 10, Line 25 - delete "he" and insert --the--

Signed and Sealed this

Tenth Day of August, 1999

Attest:

Q. TODD DICKINSON

*Attesting Officer*   Acting Commissioner of Patents and Trademarks